United States Patent [19]

de Castro et al.

[11] Patent Number: 5,139,685

[45] Date of Patent: Aug. 18, 1992

[54] BLOOD SEPARATION FILTER ASSEMBLY AND METHOD

[75] Inventors: Aurora F. de Castro, Union, Mich.; Joseph W. Fraser, Jr., Granger, Ind.; Janice L. Shultz; Surendra K. Gupta, both of Elkhart, Ind.

[73] Assignee: GDS Technology, Inc., Elkhart, Ind.

[21] Appl. No.: 675,452

[22] Filed: Mar. 26, 1991

[51] Int. Cl.5 .............................. B01D 37/00
[52] U.S. Cl. ........................ 210/767; 210/85; 210/435; 210/445; 210/446; 210/496; 210/505; 210/506; 210/509; 422/56; 422/57; 422/101; 436/169; 436/170; 436/177; 604/406
[58] Field of Search ............... 210/767, 85, 435, 436, 210/445, 446, 496, 505, 506, 508, 509; 422/56, 57, 101; 436/169, 170, 177, 178; 604/406

[56] References Cited

U.S. PATENT DOCUMENTS

| | | | |
|---|---|---|---|
| 3,448,041 | 6/1967 | Swank | 210/446 |
| 3,593,854 | 7/1971 | Swank | 210/446 |
| 3,663,374 | 5/1972 | Moyer et al. | |
| 3,791,933 | 2/1974 | Moyer et al. | |
| 4,102,785 | 7/1978 | Head et al. | 210/767 |
| 4,116,845 | 9/1978 | Swank | 210/446 |
| 4,246,107 | 1/1981 | Takenaka et al. | 210/806 |
| 4,256,693 | 3/1981 | Kondo et al. | 422/56 |
| 4,283,289 | 8/1981 | Meyst et al. | 210/448 |
| 4,330,410 | 5/1982 | Takenaka et al. | 210/767 |
| 4,416,777 | 11/1983 | Kuroda et al. | 210/446 |
| 4,477,575 | 10/1984 | Vogel et al. | 436/170 |
| 4,701,267 | 10/1987 | Watanabe et al. | 210/505 |
| 4,753,776 | 6/1988 | Hillman et al. | 422/101 |
| 4,952,516 | 8/1990 | Matkovich | 427/101 |
| 4,985,153 | 1/1991 | Kuroda et al. | 210/767 |

Primary Examiner—Robert A. Dawson
Assistant Examiner—Sun Uk Kim
Attorney, Agent, or Firm—Browdy and Neimark

[57] ABSTRACT

Blood separation filter assemblies and methods are provided to quickly and completely separate plasma or serum from whole blood without the need of centrifugation. The filter assemblies and methods have filter materials of a predetermined thickness which are maintained under positive pressure during use. The filter materials have at least one layer of glass fibers having an average fiber diameter ranging from 0.2 μm to 7.0 μm and which are compressed at least 25% in thickness.

25 Claims, 4 Drawing Sheets

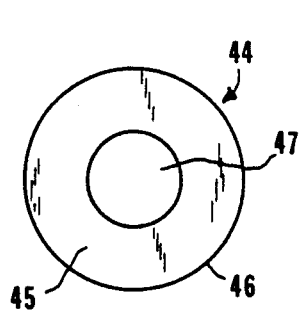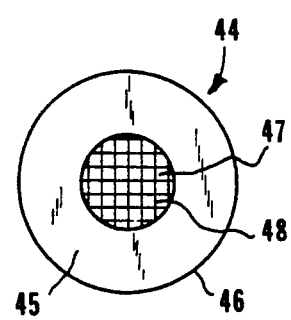
FIG. 7   FIG. 8   FIG. 9
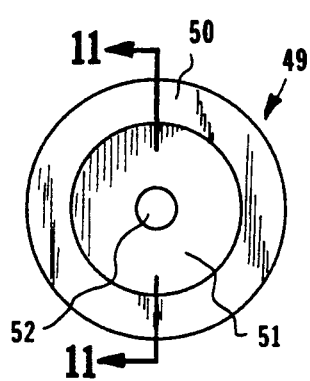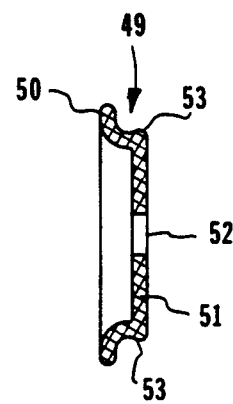
FIG. 10   FIG. 11
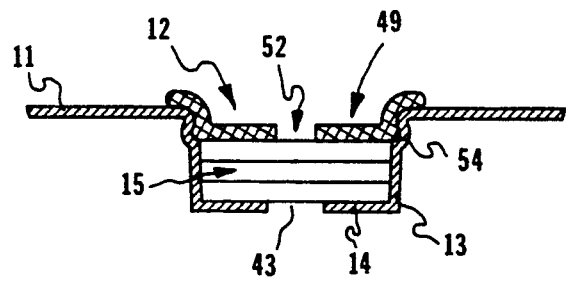
FIG. 12
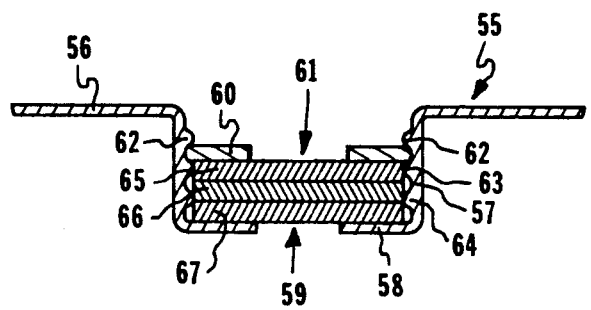
FIG. 13

BLOOD SEPARATION FILTER ASSEMBLY AND METHOD

BACKGROUND OF THE INVENTION

1. Field of the Invention

This invention relates generally to assemblies and methods for separating fluids from particulate matter and particularly to the separation of plasma or serum from blood by filtration. This invention is particularly directed to filtration assemblies using glass fibers under direct pressure resulting in compression of the glass fibers to specified densities. The high or positive pressure on the filter or filter layers is applied and maintained throughout the filtering process.

2. Description of the Background

Compounds associated with diseases or health conditions such as metabolites or drugs are often found in body fluids such as blood. Therefore, in clinical laboratories, blood is used for diagnostic determinations or tests in order to provide information about the health status of patients. Blood is comprised mainly of corpuscular or particulate matter, for example, red and white blood cells and fluid matter such as serum or plasma. Generally, in clinical laboratories, when a test for a particular blood analyte is needed, the patient's blood which has been transported to the laboratory, is first separated from the serum (blood is allowed to clot with no anticoagulants present) or plasma (blood is drawn in the presence of anticoagulants) by centrifugation. Subsequently, the plasma or serum is used for the measurement of the particular analyte using automated instrumentation. This is a time-consuming process. However, when an urgent or emergency situation arises, tests or assays need to be performed which can yield results rapidly and at the patients' site. These urgent situations cannot be satisfactorily met with tests that need transportation, automated instrumentation or highly trained personnel. Therefore, the tests or devices which can be used for on-site testing with a rapid turnaround time require a blood separation method which will permit the separation of serum or plasma from blood in less than 15 seconds and preferably in 2-10 seconds, will completely remove red blood cells, and will not be technique dependent, such as wiping or washing of red blood cells.

A number of techniques have been devised to accomplish this difficult separation. All techniques utilize a filtering step capable of separating red blood cells. Numerous materials have been used in the past as filters utilizing certain conditions, composition, and devices. Papers, non-woven fabrics, sheet-like filter material composed of powders, or fibers such as man-made fibers or glass fibers and membrane filters having suitable pore sizes have been proposed. Although glass fibers have been known in the prior art as a material used for this separation process, subsequent improvements utilizing several specific methods have been claimed to give different degrees of speed and/or completion of separation. For example, Moyer et al. uses glass fibers for filtration of blood as described in U.S. Pat. No. 3,791,933. U.S. Pat. No. 4,256,693 to Kondo et al. discloses a number of filter materials, including glass fibers, in a multi-layered integral chemical analysis element for use in blood separation. Subsequently, Vogel et al., U.S. Pat. No. 4,477,575, showed a composition and process for allowing the separation of serum from whole blood consisting of glass fibers having an average diameter of $0.2\mu$ to $5\mu$ and a density of $0.1$ gm/cm$^3$ to $0.5$ gm/cm$^3$ without applying any positive pressure and which generally takes 1 to 5 minutes for separation of plasma from blood. Subsequently, Hillman et al., in U.S. Pat. No. 4,477,575, showed a blood separation device using glass fibers to separate plasma from blood where the filtration is carried out at low pressures. The filter in this latter invention only retards the flow of red blood cells. However, these prior art techniques are not suitable where faster flow rates, for example, in less than 15 seconds and preferably in 2-10 seconds, are desired as well as the complete retention of the cells, i.e., determination of analytes needed for urgent care drug overdose cases, such as acetaminophen, theophylline, digoxin, salicylate, etc.

Despite the need for assemblies and methods to quickly separate plasma or serum from whole blood, and which overcome the limitations and problems of the prior art, none insofar as is known has been proposed or developed.

Accordingly, it is an object of the present invention to provide assemblies and methods to further refine and advance blood separation techniques.

SUMMARY OF THE INVENTION

The present invention provides assemblies and methods to quickly separate plasma or serum from whole blood. The invention provides a fast (fifteen (15) seconds or less) and simple means for completely separating plasma or serum from whole blood, not just retarding, without the need of centrifugation.

The present invention also provides a composition, process and assembly for separating red blood cells from serum or plasma which is fast (in less than 15 seconds and preferably in 2 to 10 seconds) and in which the complete separation of serum from blood under these conditions does not affect the recovery of small molecules, such as glucose, lipid molecules, such as cholesterol, or large molecules, such as enzymes (Lactate dehydrogenase etc.).

In this invention it has surprisingly been found that when it is desired to achieve separation of serum or plasma from blood, glass fibers produce the fastest flow rate when maintained in a compressed state under pressure. That is, a direct high positive pressure that produces or results in a high packing density of glass fibers which is higher than $0.5$ gm/cm$^3$, can be used to effectuate the fastest separation, i.e., in less than 15 seconds and preferably in 2 to 10 seconds. Unexpectedly, the high density of filter material, instead of slowing down the rate of filtration, increases the rate of filtration of the fluid part from the particulate part, for example, of serum or plasma from red blood cells. To effectuate complete filtration of the particulate matter under these conditions, one can use a depth of filter material of $0.04''$ or higher, while the diameter of glass filter material can vary. To attain such fast and complete separation, one must change the characteristics of commercially available material by applying significant pressure to achieve a resultant significant compression.

Furthermore, the filtration is as effective when the filtering layer, which is under pressure, comprises at least two or more separate layers of glass fiber material instead of one layer of the same total thickness. That is, when two separate layers of glass fibers, as opposed to one comparable single layer, are placed one on top of the other under pressure, the different interfaces between the separate layers do not significantly affect the separation.

A specific device and composition to carry out the process or method of the instant invention is also shown. The complete recovery of small and large molecular weight analytes including lipids utilizing the separation system of the instant invention is also demonstrated.

These and other benefits of this invention will become clear from the following description by reference to the drawings.

BRIEF DESCRIPTION OF THE DRAWINGS

FIG. 7 is a top view of a cover structure for use in the well structure of diagnostic cards and strips to contain the filter layers of this invention;

FIG. 8 is a lateral view of the cover structure of FIG. 7;

FIG. 9 is a top view of another cover structure for use in this invention;

FIG. 10 is a top view of another cover structure for use in this invention:

FIG. 11 is a sectional view taken along line 11—11 of FIG. 10;

FIG. 12 is a sectional view of another well structure designed to fit the cover shown in FIGS. 10 and 11.

FIG. 13 is a sectional view of another well structure for containing the filter assembly of this invention:

DESCRIPTION OF THE PREFERRED EMBODIMENTS

The present invention may be used in any device having means of providing and maintaining positive pressure on the glass fibers themselves, such as described in pending U.S. application Ser. No. 07/469,920, filed Jan. 24, 1990, now abandoned, and in U.S. application Ser. No. 07/628,348, filed Dec. 17, 1990, now U.S. Pat. No. 5,104,619.

Figure 1:
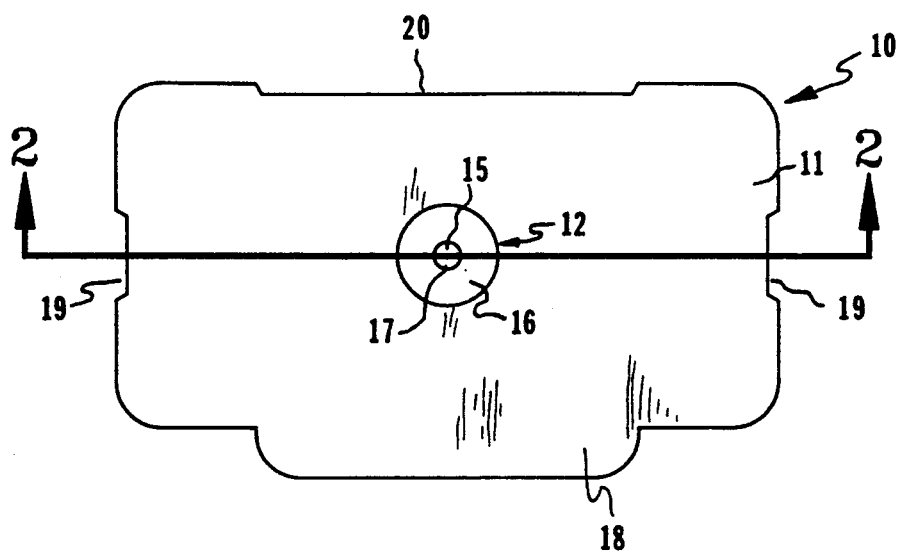
FIG. 1 is a top view of a diagnostic test card having a well structure having the filter assembly of this invention.
Figure 3:
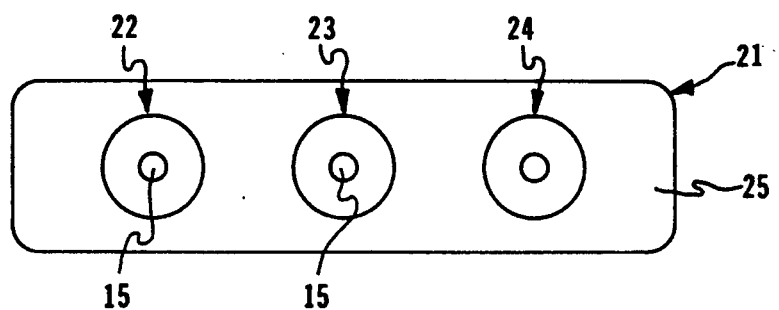
FIG. 3 is a top view of a diagnostic test strip having a plurality of well structures.

For example, FIG. 1 shows a separation filter assembly of this invention as a diagnostic card structure 10. The filter assembly 15 is shown contained in well structure 12 of a generally planar body 11. The card body 10 has alignment or positioning slots 19 and 20 and holding tab 18 to provide both for insertion of card 10 into an associated diagnostic meter for reading and for physical manipulation for observation, although these particular features are not essential for purposes of this invention. FIG. 3 shows the separation filter assembly as a diagnostic test strip 21 having planar body 25 with multiple well structures 22, 23 and 24. Any or all of these well structures may contain a filter assembly 15 for particular multiple testing purposes.

Figure 2:
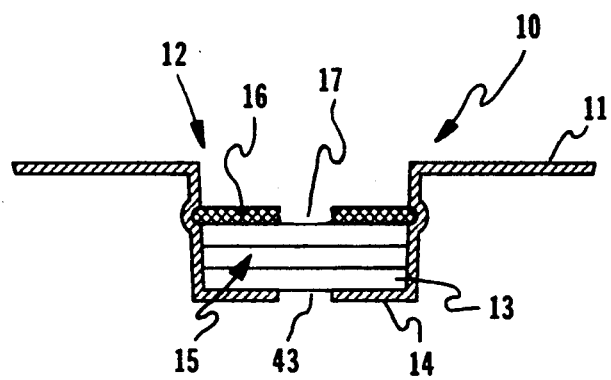
FIG. 2 is a sectional view taken along line 2—2 of FIG. 1.

FIG. 2 shows more detail of the filter assembly 15 of FIG. and showing the cylindrical well wall 13 of well structure 12. The filter assembly 15 is shown sandwiched between the retaining cover structure 16 and the well bottom 14. Importantly, the filter assembly 15 is maintained compressed in the well structure 12 to provide the fast separation of serum or plasma from a blood sample, for example, introduced through central aperture 17.

Figure 4:
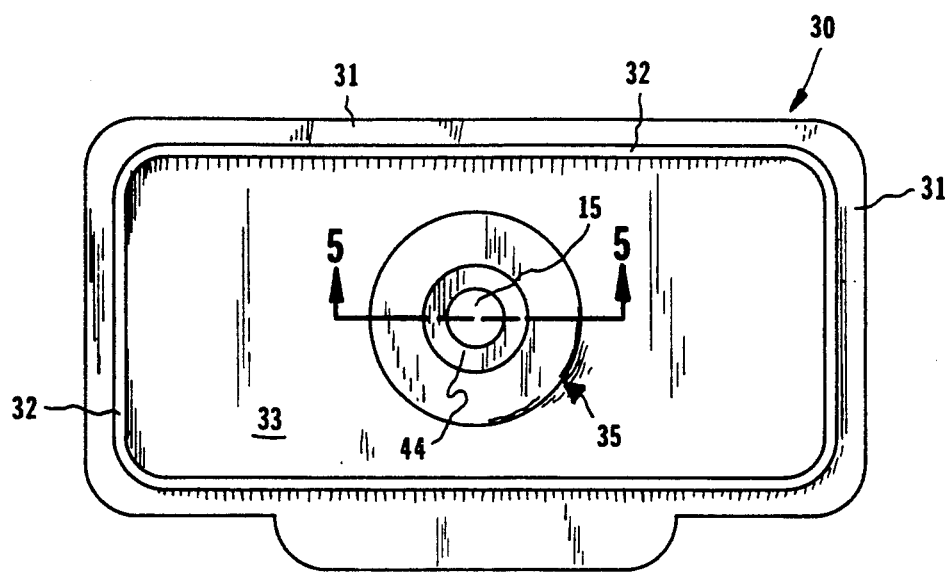
FIG. 4 is a top view of a diagnostic test card having another well structure embodiment having the filter assembly of this invention.
Figure 5:
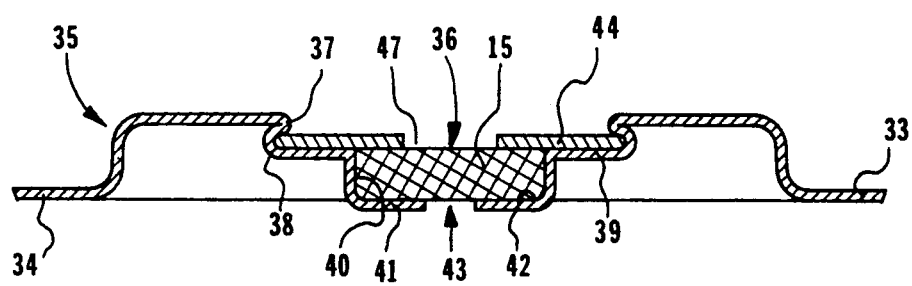
FIG. 5 is a sectional view taken along line 5—5 of FIG. 4.

FIG. 4 shows a diagnostic test card 30 having centrally located raised cylindrical portion 35 with a well 36 within which the filter assembly 15 can be placed and held in a state of compression. The well 36 is positioned vertically with respect to top surface 33 which further has a perimeter lip 31 separated by a raised rib 32, although the last two mentioned features are not essential for the instant invention. The seotional view of FIG. 5 shows the cylindrical portion 36 having a folded lip 37, annular recess 38 and an upper horizontal shelf 39 which defines the well 36 as shown by well wall 40 and well bottom 41. The filter assembly 15 is contained within the well wall 40 and between the bottom upper surface 42 and a retaining structure, such as a snap fit cover 44 (FIGS. 7-9), cover 49 (FIGS. 10 and 11) or similar means which may be snapped within the annular recess 38 of card 30, for example.

FIGS. 7-11 illustrate compression and retaining structures for the filter assemblies of the diagnostic card and strip wells. FIGS. 7-9 show a flat snap fit lid or cover 44 having a circular body 45, outer edge 46 and a central aperture 47 to receive the fluid or blood sample for separation. A grid structure 48 may span the aperture 47 to aid in compressingly engaging the filter assembly 15. A different configuration of lid or cover, which is not flat, is shown in FIGS. 10 and 11, showing cylindrical cover 49 having outer circumferential lip 50, top portion 51 and aperture 52. Tapered side wall 53 is provided to snap into folded lip 37 and annular recess 38 with slightly different shape of that shown in FIG. 5 to, thereby, maintain the filter assembly 15 in a predetermined compressed state. A slightly different shape of the well having annular ridge 54 and associated lid 49 are shown in FIG. 12. FIG. 13 shows another means to compress and maintain a filter assembly for purposes of this invention. A well structure 55 has a body 56 with a well bottom 58 and cylindrical wall 57 having a number of interior adjustment ridges 62, 63 and 64 between which a retaining structure or cover 60 can be adjustably fixed to compressingly hold filter layers 65, 66 and reagent layer 67. A blood sample is introduced through aperture 61 and the test result is read through aperture 59, for example. Alternatively, another device could be used and made in the shape of a long rigid plastic strip on which the filter layer(s) and reactive layer are placed and compressed together by means of a strong adhesive tape to provide the positive pressure.

Figure 6:
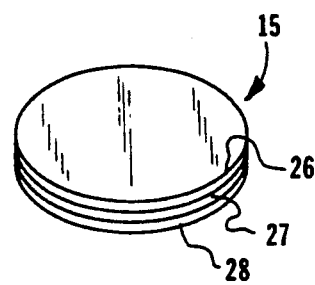
FIG. 6 is a perspective view of a filter layer structure of this invention.

The filter assembly compositions and arrangement will be described with further particularity, in the Tables and Examples set forth hereafter. However, FIG. 6 illustrates a filter assembly 15 having fiber filter layers 26 and 27 and a lower reagent impregnated layer 28, for example, to produce a measurable signal. As will be discussed, various layer combinations including specific filter layer and reagent layers are usable to provide the filter assemblies and separation methods of this invention.

Figure 14:
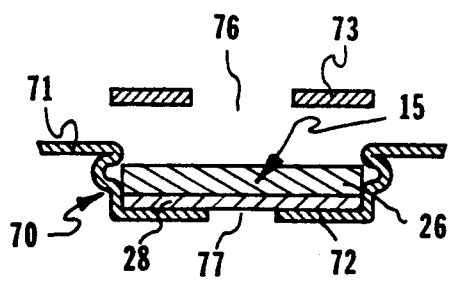
FIG. 14 is a sectional view of an uncompressed filter assembly placed in a well structure.
Figure 15:
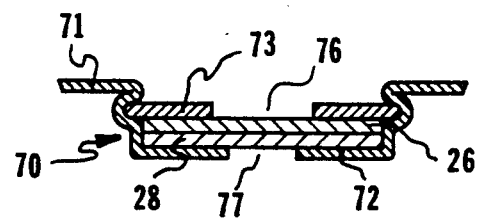
FIG. 15 is a sectional view of the filter assembly of FIG. 14 held compressed in the well structure.
Figure 16:
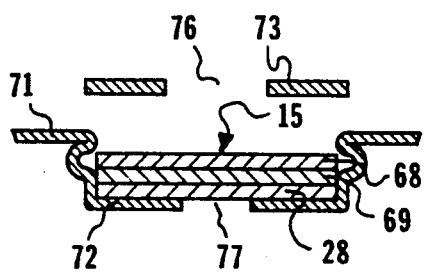
FIG. 16 is a sectional view of another uncompressed filter assembly placed in a well structure.
Figure 17:
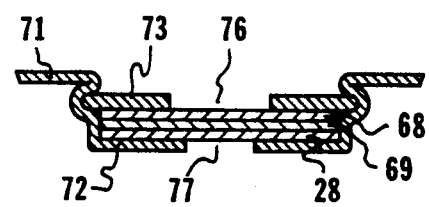
FIG. 17 is a seotional view of the filter assembly of FIG. 16 held compressed in the well structure.

FIG. 14 shows a filter assembly 15 of FIG. 6 having only one filter layer 26 and a reagent impregnated layer 28 contained in well structure 70 of card structure 71. The filter assembly 15 is placed on well bottom 72 and the filter layer 26 is shown in its uncompressed state. FIG. 15 shows the cover member 73 positioned in the well structure 70 whereby the filter layer 26 is held compressed by the cover member 73. FIG. 16 shows the filter assembly 15 having two filter layers 68 and 69. As shown in FIG. 17, the positioning of the cover member 73 into the well shows the filter layers 68 and 69 being compressed. As further shown, the filter layers 68 and 69, when combined, have the same thickness as that of single filter layer 26.

In summary, the wells or pockets of the above structures confine the filter materials or glass fiber filter layers and associated matrices which contain reagents to produce measurably signals to indicate the presence of an analyte, for example. The rigid lids or covers 73 of the structures of FIGS. 14–17 are in direct contact with the filter assemblies and are used to apply positive pressure and compression of the respective filter layers within the wells 70 to provide a higher packing density than the original or uncompressed material density. That is, in these devices the pressure on the glass fiber filters or membranes are applied and maintained by the rigid covers or lids 73 which are snapped into the respective wells 70 wherein the filter assemblies are contained. Thus, when the lid 73 is snapped into the well groove, the effective well depth for the compressed material is the space between the well bottom 72 and the snapped in top 73 regardless of the dimension of the well depth. As shown, the device can contain a lower reagent layer 28 to provide the necessary chemicals to react with the serum or plasma. In use, a blood sample is introduced into aperture 76 and read at bottom aperture 77.

Figure 18:
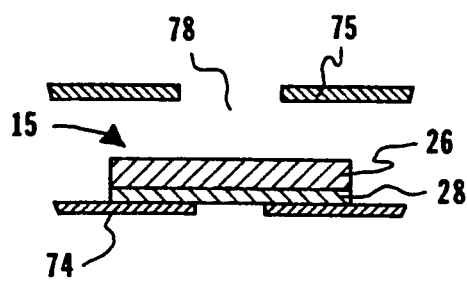
FIG. 18 is a sectional view of a filter assembly placed on a base structure.
Figure 19:
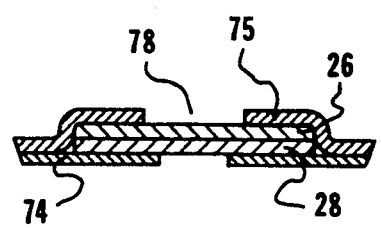
FIG. 19 is a sectional view of the filter assembly of FIG. 18 held compressed onto the base structure according to the teachings of this invention.

FIG. 18 shows an alternate structure where the filter assembly 15 is placed on top of a rigid base structure 74, such as a piece of rigid or semi-rigid plastic. FIG. 19 shows positive pressure applied to the filter assembly 15 by means of a strip of adhesive tape 75 which is shown to compress the filter layer 26 according to the teachings of this invention. The tape piece 75 has an aperture 78 for addition of a blood sample. The base structure 74 could be clear plastic so that any reaction can be visualized therethrough. Alternatively, an aperture may be provided in the base structure 74 for visualization or meter reading purposes. Any other devices or assemblies that can exert positive pressure and, therefore, compress the glass fibers into a higher packing density can be used to practice this invention.

One important aspect of the invention is that separation of red blood cells from plasma can be accomplished in less than 15 seconds utilizing layers of glass fiber filter material with a small volume of blood, for example, 10–65 μl. The invention can be carried out by taking selected commercially available material(s) and modifying them sufficiently by pressure. However, many prior art or commercially available materials used for blood separation have proven not to be useful for the desired separation required and taught by this invention. The present invention allows the application of whole blood directly to the side of the device in contact with the glass fibers, and the fast observation, from the opposite side, of the reactions produced by the desired analyte present in the blood sample. Separation of the red cells is achieved mainly as a result of mechanical retention of particles. However, because of the irregular size and shape of the commercially available glass fibers, it is not possible to determine or specify a defined pore size for such filters.

Commercially available glass fibers are often made of a high percent borosilicate glass and are composed of irregular filtering fibers typically varying in diameter between 0.1 μm and 7.0 μm. A key feature of the present invention is that the separation can be made independently of the diameters of the fibers provided that the positive pressure is high enough to compensate for low diameter fibers by increasing the packing density appropriately. For example, with some of the large diameter fibers a packing density of 0.60 gm/cm$^3$ can be successfully used, while with some of the small diameter fibers a packing density of 0.85 gm/cm$^3$ may be necessary to achieve the same separation. In all cases, a minimum depth of glass filters of 1 millimeter (0.04") was found desirable.

A number of commercially available glass fiber filters or membranes can be utilized with the invention, but not all, to keep with the practical constrains of the invention, for example, sample size. Numerous glass fibers were tested for the purpose of this invention from various commercial sources as described in Table 1:

TABLE 1

| COMPANY | FILTER NUMBER |
| --- | --- |
| Millipore Corporation Bedford, Mass. | AP-15, AP-20, AP-25, AP-40 |
| Whatman, Inc. | GF/C, GF/B, GF/D, GF/F, 934-H |
| Clifford, N.J. | PD 00823B143, PD813C120 |
|  | PD 00812c53, PD008-11 |
| Ahlstrom (Mount Holly Springs, PA) | AHLSTROM 153, AHLSTROM 113 |
| Schliecher & Schuell (Keene, NH) | S & S 24, S & S 30, S & S 20 (3362) S & S 25 |
| Microfiltration Systems (MFS) (Dublin, CA) | GA-200, GB-100R, GC-90 |
| Hollingsworth & Vost East Walpole, MA | HB-5342, BG-08805 |
| Eaton Dikeman (now Ahlstrom) Carlisle, PA | 111, 121, 131, 141, 151, & 161 |
| Mechery & Nagel Duren, W.G. | 85/90F |

These glass fiber filters were tested individually, and in combination with one another, for their ability to effect the separation of serum or plasma from blood. For most of the examples the devices shown in FIGS. 1, 4 and 19 were used. However, the devices of FIGS. 1 and 4 can produce more consistent pressure on the glass fiber layers and are easier to use. The effectiveness of positive pressure, which increases the packing density of glass fibers to higher than 0.5 gm/cm$^3$, in producing better and faster separation of blood by using one or more glass fiber layers is clearly demonstrated in Examples 1–5. Analytical recovery section further demonstrates that using the device and the method of the instant invention, complete recovery of analytes with vastly different molecular weights or lipid composition can be achieved.

EXAMPLE 1

The importance of positive high pressure provided on glass fibers in altering the speed of filtration of serum or plasma from whole blood and the complete removal of Red Blood Cells (RBC) is clearly demonstrated in this example.

In this experiment, a device as shown in FIG. 1 was used. The device consists of a flat card containing a well 12 which has a diameter of 0.25" and a groove placed at a depth of 0.045". All the filter matrices or membranes used here were cut into 0.219" circles and were placed in the well. The bottom of the well has a hole of 0.156" to observe the change visually or to read the change with a reflectance meter. The lid or top 16 has a diameter of 0.25", a thickness of 0.03" and a hole of 0.156" which fits very tightly in the groove of the well.

To test the effect of positive pressure in removal of RBC's from serum, the following experiment was performed. The control experiment was set up which consisted of placing one type of glass fibers layers, as shown in the following Table 2, with a total thickness or depth of 0.09" on a Whatman 54 layer used as the reactive layer which has a thickness of about 0.005". No lid was placed in the device. Sixty-five (65) microliters ($\mu$l) of freshly drawn blood was placed on the top of the glass fibers. A second experiment was performed with the same procedure as mentioned above except that the lid was placed in the groove located at the top of the well. As the effective well depth is only 0.045", the glass fibers, in the latter case, were compressed. Sixty-five (65) $\mu$l of freshly drawn blood was also applied. The appearance of serum on Whatman 54 was observed visually as indicated by complete wetness of Whatman 54 paper. The Whatman paper was additionally observed for the appearance of red blood cells. This layer was, furthermore, monitored several minutes to assure that the red blood cells were not just retarded. Table 2, column 1, describes various glass fibers used in this experiment with a total thickness of 0.09". To obtain this total thickness, two layers of AP-25 (Millipore Co.), each of 0.045"0 thickness, were used and nine layers of AP-20 (Millipore Co.), each of 0.01", were used. Column 2 shows the time required to wet the bottom pad. Column 3 describes either the presence of RBC's observed on Whatman 54 paper by (+) sign, or complete absence of RBC's observed by (−) sign, immediately, as well as at the end of ten (10) minutes. In this example, the density of compressed material was in the range of 0.7–4.0 gm/cm$^3$.

TABLE 2

| Glass Fiber Configuration | Time to Wet Bottom Pad | Presence (+)/ Absence (−) of RBCs |
|---|---|---|
| AP-25 | | |
| with lid | 11–13 second | (−) |
| without lid | >360 seconds | (−) |
| AP-20 | | |
| with lid | 255 seconds | (−) |
| without lid | Did not permeate at all | |

The results obtained were the same when whole blood in the presence of anticoagulant was used.

EXAMPLE 2

The material and methods of this example were the same as in Example 1 except that two different types of glass fibers were used to make up the total thickness of 0.09" within the well. In one case, a combination of two S&S 24 and one S&S 30 were used. In the second case, a combination of one AP-25 and four AP-20 were used. The bottom layer was observed for time or speed (sec.) of wetting. The beneficial effect of positive pressure on the fastness of the separation when two types of glass fibers are used in combination, is demonstrated in Table 3. The observation for the presence or absence of RBC's was repeated after ten (10) minutes. In this example, the density of compressed material was 0.8–2.8 g/cm$^3$.

TABLE 3

| Glass Fiber Configuration | Time to Wet Bottom Pad | Presence (+)/ Absence (−) of RBCs |
|---|---|---|
| Two S & S 24 and One S & S 30 | | |
| with lid | 8–9 seconds | (−) |
| without lid | Did not permeate at all | |
| One AP-25 and Four AP-20 | | |
| with lid | 11 seconds | (−) |
| without lid | Did not permeate at all | |

EXAMPLE 3

To increase the speed and efficiency of the blood separation, the thickness of the filtering materials was reduced to 0.06". The device of Example 1 was used except that the effective well depth was different, i.e., the distance between the bottom of the lid when snapped in the groove and the bottom of the well was 0.04". In this case, the glass fiber filter was a combination of one AP-25 and one AP-20 layer. Fifty-five microliters (55 $\mu$l) of freshly drawn blood was applied to the device with and without the lid and the time for separation was measured. Table 4 demonstrates that the speed of separation was further increased to 2–5 seconds. The observation to determine if blood cells came through was extended to ten (10) minutes. The application of the lid increased the packing density more than 30% in this configuration resulting in a compressed density material of about 0.6 gm/cm$^3$.

TABLE 4

| Glass Fiber Configuration | Time to Wet Bottom Pad | Presence (+)/ Absence (−) of RBCs |
|---|---|---|
| One AP-25 and One AP-20 | | |
| with lid | 2–5 seconds | (−) |
| without lid | >30 seconds | (+) |

EXAMPLE 4

To decrease the blood volume required for the blood separation and subsequent testing, the diameter of the well in the device of FIG. 1 was reduced to 0.219". Therefore, the diameter of the filtering matrices was also reduced to 0.187" circles. The effective depth of the well, i.e., the distance between the snapped lid and the bottom of the well was 0.04". Thirty microliters (30 $\mu$l) of freshly drawn blood was applied to the top glass fiber filters which was a combination of one AP-25 and one AP-20 filters and a reactive layer of Whatman 54 with and without the lid, and the time for separation was measured. Table 5 demonstrates that the speed of separation was the same as in Example 3, i.e., 2–5 seconds in presence of the lid or under conditions of pressure. The observation to determine if red blood cells came through was extended to ten (10) minutes. The application of the lid increased the packing density by more than 30% in this configuration resulting in a compressed material density of about 0.6 gm/cm$^3$.

TABLE 5

| Glass Fiber Configuration | Time to Wet Bottom Pad | Presence (+)/ Absence (−) of RBCs |
|---|---|---|
| One AP-25 and One AP-20 | | |
| with lid | 2–5 seconds | (−) |
| without lid | >30 seconds | (+) |

The same experiment was repeated using blood with anticoagulant present and the device of FIG. 18 with similar results.

EXAMPLE 5

In another experiment utilizing the device dimensions of Example 3, the following combination of glass fibers shown in Table 6, also showed separation times of less than ten (10) seconds when 55 μl of blood was applied to the surface of glass fibers and separated under positive pressure. In this experiment, the compression resulted in higher than 25% compression of glass fibers with a density of more than 0.5 gm/cm$^3$.

TABLE 6

| Glass Fiber Configuration with 0.01" reagent pad | Thickness before compression | Time to Wet Bottom Pad | Presence (+)/ Absence (−) of RBCs |
|---|---|---|---|
| Two GF/D with lid | 0.06" | 5–7 seconds | (−) |
| One MFS GA-200 with lid | 0.045" | 2–3 seconds | (−) |
| Two MFS GB-100R with lid | 0.052" | 4–5 seconds | (−) |

It is evident from the above examples that the instant invention achieves the complete separation or filtration of plasma or serum from blood with a speed of less than 15 seconds, preferably in 2–5 seconds, when positive or high pressure is applied. In all cases, the glass fibers need to be compressed more than 25% of the original thickness or depth to produce a density of higher than 0.5 gm/cm$^3$ and need to have a minimum depth or thickness of 0.04" (1 millimeter) in order to obtain complete separation. The extremely fast separation achieved is not a retardation of red blood cells as shown by the fact that even after ten (10) minutes no red blood cells came through. This process of separation can be achieved with any device similar to the ones shown in the drawing figures where positive pressure can be applied.

ANALYTE RECOVERY AFTER EXPOSURE TO GLASS FIBER FILTRATION

Experiments were performed to determine if glass fibers under high pressure could be used in determination of various analytes in blood by measuring recovery of these analytes.

Blood samples were obtained by drawing the patient's blood into glass Vacutainer ® tubes. Blood samples were used for the analytical determination of metabolites such as Glucose, Cholesterol, and enzymes such as Lactate dehydrogenase. The blood samples used for the determination of other analytes and drugs such as B-hydroxybutyrate, acetaminophen or theophylline were spiked gravimetrically with the particular analyte under investigation. Part of each blood sample was centrifuged after letting it stand at room temperature for 20 minutes and serum was thus obtained. The serum was split into two aliquots for the following experiments.

For each analyte measurement, the device as described in Example 4 was used. The first serum aliquot, 30 μl, was placed at the aperture of the cover of the device containing glass fiber filters, such combination of AP-25 and AP-20 (compressed by the snap fit cover), and a bottom reactive layer 28 which was impregnated with the necessary ingredients (i.e. chemicals known in the prior art which react with the particular analyte and which produce color proportionate to the concentration of analyte present in the sample) and dried at 50° for 5 minutes. The second serum aliquot was directly placed on the reactive layer of a second device which did not contain glass fiber filters. In both cases, the color produced in the reactive layer was measured as reflectance by a Macbeth reflectance meter at a fixed time. For each analyte, the reflectance value in both situations compared within 93–106% of each other. These results clearly show that the glass fiber filters did not retain any of the analytes tested.

Furthermore, an aliquot of the same whole blood, 30 μl, which was not centrifuged was placed on a third device, as described in Example 4, consisting of glass filters such as a combination of AP-25 and AP-20 (compressed by a snap fit cover), and the same reactive bottom layer 28. The reflectance produced by the color at the bottom layer was compared with the reflectance value obtained in the first device where serum was used. As demonstrated in Table 7, the analytes' recovery were 94–106% when blood was compared to serum irrespective of the molecular weight (from 113 to 140,000) of the chemical tested, or composition of the analyte (lipid or protein). In these experiments, a complete removal of RBCs was observed and the separation of serum from blood using glass fibers under positive pressure took place in 2–5 seconds.

These experiments clearly show that whole blood can be successfully used with these devices and methods of the present invention, and is interchangeable with serum; in the determination of small molecular weight analytes such as glucose, B-hydroxybutyrate, lipid molecules such as cholesterol, drug concentration in blood such as theophylline and acetaminophen, as well as high molecular weight proteins or enzymes such as lactate dehydrogenase (LDH).

TABLE 7

| Analyte | Molecular Weight | % recovery of the analyte blood/serum |
|---|---|---|
| Glucose | 180 | 95–105 |
| β-hydroxybutyrate | 113 | 95–102 |
| Cholesterol (Lipids) | 386 | 95–105 |
| Acetaminophen | 151 | 98–101 |
| Theophylline | 180 | 95–105 |
| Lactate dehydrogenase | 140,000 | 94–106 |

It will be understood that the descriptions, drawings and examples are illustrative but not limitative of the present invention and that other embodiments and processes within the spirit and scope of the invention will suggest themselves to those skilled in the art.

That which is claimed is:

1. A filter assembly having filter material of a predetermined thickness under positive pressure for the fast separation of serum or plasma from whole blood, comprising at least one layer of glass fibers having an average diameter ranging from 0.2 μm to 7.0 μm and means to compress said filter material whereby said filter material is compressed at least 25% in thickness and to a compressed density higher than 0.5 gm/cm$^3$.

2. The filter assembly of claim 1, wherein said filter assembly is further comprised of a diagnostic card having a well structure and wherein said filter material compression means is comprised of a snap-fit cover for securing said filter material in said well under constant pressure.

3. The filter assembly of claim 1, wherein said filter material has a total thickness of at least 0.04 inches and wherein said filter material is capable of filtering a volume of greater than 0 μl and less than 65 μl of blood in less than 15 seconds.

4. The filter assembly of claim 1, wherein said glass fibers are comprised of borosilicate glass.

5. The filter assembly of claim 1, wherein said glass fiber material consists of at least two separate filter layers.

6. The filter assembly of claim 1, wherein said filter material permits the passage of analytes present in blood, said analytes ranging from having a molecular weight of 30 to 2000 to proteinous substances having a molecular weight of over 5,000.

7. A clinical diagnostic device containing filtration material under positive pressure wherein said filtration material is capable of separating serum or plasma from a specified volume of whole blood in less than 15 seconds, said filtration material comprising:
   a) glass fibers having an average diameter ranging from 0.2 μm to 7.0 μm;
   b) being in a compressed state of at least 25% of its uncompressed state; and
   c) a compressed thickness of at least 0.04".

8. The diagnostic device of claim 7, wherein said compressed filtration material has a packing density of at least 0.5 gm/cm$^3$.

9. The diagnostic device of claim 7, wherein said specified volume of whole blood is greater than 0 μl and less than 65 μl.

10. The diagnostic device of claim 7, wherein said glass fibers are comprised of borosilicate glass.

11. The diagnostic device of claim 7, wherein said filtration material is comprised of at least two separate types of glass fiber layers.

12. In a clinical diagnostic device having a body, a pocket for containing filtration materials to separate an analyte, closure means to close said pocket, and inlet means to receive a fluid sample into said pocket, said filtration materials comprising:
   a) at least one layer of glass fibers and having a total thickness of at least 0.04";
   b) said glass fibers having an average diameters of 0.2 μm to 7.0 μm;
   c) said closure means being constructed and arranged to compress said glass fibers at least 25% by the application of positive pressure and to result in the glass fibers having packing density of at least 0.5 gm/cm$^3$; and
   d) a reactive layer in contact with said filtration material for determination of an analyte.

13. The diagnostic device of claim 12, wherein said fluid sample is whole blood and wherein said filtration material is capable of filtering the serum or plasma of a volume of greater than 0 μl and less than 65 μl of blood in less than 15 seconds.

14. The diagnostic device of claim 12, wherein said glass fibers are comprised of borosilicate glass.

15. The diagnostic device of claim 12, wherein said filtration material is comprised of at least two separate types of glass fiber layers.

16. A process for the fast separation of serum or plasma from whole blood, comprising:
   a) providing a filtration assembly having a well of a predetermined depth, a cover for said well and means to introduce whole blood into said well;
   b) placing at least one glass fiber filter layer into said well, said glass fibers of said filter layer having an average diameter ranging from 0.2 μm to 7.0 μm;
   c) placing said cover into said well and compressing said glass fiber filters at least 25%;
   d) securing said cover in said well to maintain said glass fibers in said compressed state; and
   e) introducing whole blood into said well for the fast separation of serum or plasma.

17. The process of claim 16, wherein said process is used in the determination of an analyte present in blood from a group of analytes ranging from a small molecular weight of 30 to 2000 to proteinous substances having a high molecular weight over 5,000.

18. The process of claim 16, wherein said means to introduce whole blood into said well is comprised by providing an aperture in said cover.

19. The process of claim 16, wherein said compressed glass fibers are capable of filtering a volume sample of greater than 0 μl and less than 65 μl of blood in less than 15 seconds.

20. A process for the fast and complete separation of serum or plasma from a whole blood sample, comprising:
   a) providing a separation filter assembly having sample inlet means, a well structure and a cover member;
   b) introducing a filter material comprised of glass fibers into said well structure;
   c) compressing said glass fibers at least 25% of their uncompressed thickness in said well structure by means of introducing and securing said cover into said well structure to thereby compress said glass fibers to a thickness of not less than 0.04" and to a density of at least 0.5 gm/cm$^3$; and
   d) introducing a whole blood sample into said inlet means for separation.

21. The process of claim 20, wherein said cover member provided is a snap-fit cover and wherein said inlet means is an aperture in said snap-fit cover.

22. The process of claim 20, wherein said glass fibers provided are comprised of borosilicate glass.

23. The process of claim 20, wherein said glass fiber material provided consists of at least two separate filter layers.

24. The process of claim 20, wherein said filter material provided permits the passage of analytes present in blood, said analytes ranging from having a molecular weight of 30 to 2000 to proteinous substances having a molecular weight of over 5,000.

25. The process of claim 20, wherein a volume sample of greater than 0 μl and less than 65 μl of blood is filtered in less than 15 seconds.

* * * * *